US012324507B2

(12) United States Patent
Jungnickel et al.

(10) Patent No.: US 12,324,507 B2
(45) **Date of Patent: *Jun. 10, 2025**

(54) PERSONAL CARE GUIDANCE SYSTEM AND MAGNETIC PERSONAL GUIDE

(71) Applicant: The Gillette Company LLC, Boston, MA (US)

(72) Inventors: Uwe Jungnickel, Königstein im Taunus (DE); Olaf Sörensen, Mainz (DE); Lance Ataalla, Hattersheim am Main (DE)

(73) Assignee: The Gillette Company LLC, Boston, MA (US)

( * ) Notice: Subject to any disclaimer, the term of this patent is extended or adjusted under 35 U.S.C. 154(b) by 90 days.

This patent is subject to a terminal disclaimer.

(21) Appl. No.: 18/315,535

(22) Filed: May 11, 2023

(65) Prior Publication Data

US 2023/0368881 A1 Nov. 16, 2023

(30) Foreign Application Priority Data

May 13, 2022 (EP) .................................... 22173186
Apr. 6, 2023 (EP) .................................... 23167103

(51) Int. Cl.
*A46B 17/00* (2006.01)
*A46B 5/00* (2006.01)
(Continued)

(52) U.S. Cl.
CPC ............ *A46B 17/00* (2013.01); *A46B 5/0095* (2013.01); *A46B 15/0008* (2013.01);
(Continued)

(58) Field of Classification Search
CPC ... A46B 17/00; A46B 5/0095; A46B 15/0008; A46B 15/0026; A46B 15/0038;
(Continued)

(56) References Cited

U.S. PATENT DOCUMENTS 5,163,566 A * 11/1992 Hempel .................. A47K 1/09 211/DIG. 1
5,864,288 A * 1/1999 Hogan ............... A46B 15/0002 340/568.1

(Continued)

FOREIGN PATENT DOCUMENTS

JP H0582321 U 11/1993
KR 20190112889 A 10/2019

OTHER PUBLICATIONS

U.S. Appl. No. 18/315,545, filed May 11, 2023, to Uwe Jungnickel et al.

(Continued)

*Primary Examiner* — Zhen Y Wu
(74) *Attorney, Agent, or Firm* — Jay A. Krebs

(57) ABSTRACT

A personal care guidance system for guiding a user through a personal care routine, the system including a personal care implement having a section at least partially made from a magnetic and/or ferromagnetic material, and a magnetic personal care guide to which the personal care implement is magnetically attachable and detachable. The magnetic personal care guide includes a guidance tool, the guidance tool being activated by detaching the personal care implement from the magnetic personal care guide.

15 Claims, 5 Drawing Sheets

(51) Int. Cl.

| | |
|---|---|
| ***A46B 15/00*** | (2006.01) |
| ***A46B 17/08*** | (2006.01) |
| ***F16M 13/02*** | (2006.01) |
| ***G04F 1/00*** | (2006.01) |
| ***G08B 7/06*** | (2006.01) |
| ***G08B 21/24*** | (2006.01) |
| ***G16H 20/00*** | (2018.01) |
| *A47K 1/09* | (2006.01) |

(52) U.S. Cl.

CPC ...... *A46B 15/0026* (2013.01); *A46B 15/0038* (2013.01); *A46B 15/004* (2013.01); *A46B 15/0044* (2013.01); *A46B 15/0046* (2013.01); *A46B 15/0095* (2013.01); *A46B 17/08* (2013.01); *F16M 13/02* (2013.01); *G04F 1/005* (2013.01); *G08B 7/06* (2013.01); *G08B 21/24* (2013.01); *G16H 20/00* (2018.01); *A46B 2200/1066* (2013.01); *A47K 1/09* (2013.01)

(58) Field of Classification Search

CPC .............. A46B 15/004; A46B 15/0044; A46B 15/0046; A46B 15/0095; A46B 17/08; A46B 2200/1066; G16H 20/00; F16M 13/02; G04F 1/005; G08B 7/06; G08B 21/24; A47K 1/09

USPC .......................................................... 340/540

See application file for complete search history.

(56) References Cited

U.S. PATENT DOCUMENTS

| | | | | |
|---|---|---|---|---|
| 11,337,785 | B2 * | 5/2022 | Ortins | A61C 17/221 |
| 2007/0220754 | A1 * | 9/2007 | Barbaro | A45D 27/29 30/41 |
| 2008/0109973 | A1 * | 5/2008 | Farrell | A61C 17/224 15/4 |
| 2009/0070949 | A1 * | 3/2009 | Sagel | A46B 11/0058 15/28 |
| 2009/0262606 | A1 * | 10/2009 | Trost | A46B 15/0002 368/10 |
| 2010/0281636 | A1 * | 11/2010 | Ortins | A46B 15/0006 15/4 |
| 2012/0112018 | A1 * | 5/2012 | Barry | H01F 7/0252 248/206.5 |
| 2013/0015201 | A1 * | 1/2013 | Lohmann | A46B 15/0055 222/78 |
| 2013/0125326 | A1 * | 5/2013 | Schmid | A61C 17/221 15/105 |
| 2016/0157598 | A1 * | 6/2016 | Anelevitz | A46B 15/0048 368/1 |
| 2016/0296078 | A1 * | 10/2016 | Beckerman | A46B 9/04 |
| 2017/0318954 | A1 * | 11/2017 | Nishiura | A61C 17/22 |
| 2018/0256430 | A1 * | 9/2018 | Zachar | A46B 15/0053 |
| 2019/0070326 | A1 * | 3/2019 | Xie | A61L 2/26 |
| 2021/0259818 | A1 | 8/2021 | Jungnickel et al. | |
| 2022/0240661 | A1 * | 8/2022 | May | A46B 13/00 |

OTHER PUBLICATIONS

All Office Actions; U.S. Appl. No. 18/315,534, filed May 11, 2023.
All Office Actions; U.S. Appl. No. 18/315,541, filed May 11, 2023.
All Office Actions; U.S. Appl. No. 18/315,545, filed May 11, 2023.
All Office Actions; U.S. Appl. No. 18/315,552, filed May 11, 2023.
PCT Search Report and Written Opinion for PCT/US2023/021434 dated Jun. 22, 2023, 13 pages.
U.S. Appl. No. 18/315,534, filed May 11, 2023, to Peter Leonard Middleton et al.
U.S. Appl. No. 18/315,541, filed May 11, 2023, to Uwe Jungnickel et al.
U.S. Appl. No. 18/315,552, filed May 11, 2023, to Uwe Jungnickel et al.

* cited by examiner

PERSONAL CARE GUIDANCE SYSTEM AND MAGNETIC PERSONAL GUIDE

FIELD OF THE INVENTION

The present disclosure is concerned with a personal care guidance system for guiding a user through a personal care routine, the personal care guidance system comprising a personal care implement comprising a section at least partially made from a magnetic and/or ferromagnetic material, and a magnetic personal care guide to which the personal care implement is magnetically attachable and detachable. The present disclosure is further concerned with a magnetic personal guide, the magnetic personal guide guiding a user through a personal care routine.

BACKGROUND OF THE INVENTION

Systems for guiding users through personal care routines, like toothbrushing or shaving, are well known in the art. Usually, guidance is provided by means of written user instructions, videos or animations. For example, user instructions typically instruct users when a device or implement for performing a personal care routine shall be exchanged. However, in the past it has been seen that users frequently forget to exchange the device/implement, or do not even track the time of usage at all. This applies in particular to toothbrushes/toothbrush heads used for brushing teeth and shavers/shaver cartridges used for removing hair. After a certain period of use time, a personal care implement is typically worn out. Toothbrush bristles splay away, reducing brushing efficiency, and shaver blades become dulled, reducing shaving comfort. If such worn-out devices/personal care implements are not replaced by a fresh one, user experience during the personal care routine suffers. In some instances, the health of the user may be negatively affected. For example, dulled blades may cause injuries during shaving, and worn-out toothbrushes/bristles may lead to insufficient plaque removal during toothbrushing, causing gingivitis in some instances.

In relation to oral care routines, like toothbrushing, manual or powered, e.g. battery driven toothbrushes, are typically used and well known in the art. Generally, tufts of bristles for cleaning teeth are attached to a bristle carrier or mounting surface of a brush head intended for insertion into a user's oral cavity. A handle is usually attached to the head, which handle is held by the user during brushing. The head is either permanently connected or repeatedly attachable to and detachable from the handle.

In order to clean teeth effectively, appropriate brushing techniques have to be applied, including sufficiently long brushing and polishing of all teeth within the mouth. If teeth are not brushed for a sufficient period of time, this results in reduced plaque removal efficiency on teeth surfaces. However, in order to achieve and preserve good oral health, and to prevent gingivitis, it is important to clean teeth and gums thoroughly, in particular in hard to reach areas, e. g. in the region of the back molars.

Dentists usually recommend brushing teeth for at least two minutes, twice per day. However, it has been seen in the past that users typically brush their teeth over a much shorter period of time, in particular if manual toothbrushes are used. Also, dentists typically recommend to exchange a toothbrush after three months of use.

Methods for tracking users toothcare activities are known, such methods typically comprise receiving video images of a user's face during a toothbrushing session, and are, thus, relatively complex and not suitable for the use of manual toothbrushes. Also, external timers tracking the user's brushing time are known, however, such timers usually require a microcontroller comprising a wireless module providing a connection between the toothbrush and the timer. Again, such timers are relatively complex and not suitable to be used in connection with manual toothbrushes. Generally, toothbrush guiding devices or devices guiding a user through a personal care routine provide either no feedback to a user, or require incorporation of a smartphone app or other sophisticated technologies which render the guiding devices complex and expensive.

Moreover, after use of an oral care implement/after brushing the teeth, the user usually stores the wet implement/brush in a toothbrush beaker for drying. However, in a classical toothbrush beaker, drained fluids get collected and accumulated at the bottom of the beaker, and, the fluids stay in contact with the toothbrush for a longer period of time. Since the beaker is open on one side only, the toothbrush dries relatively slowly. Bacteria living in wet conditions/in a wet environment can grow quickly, contaminate the toothbrush and finally render the brush unhygienic. Consequently, there exists a need for a solution for not only guiding a user through an oral/personal care routine, but also for hygienically storing and drying a toothbrush/personal care implement, thereby enabling remaining water, toothpaste slurry and saliva to drain off from the implement. The implement shall dry quickly thereby inhibiting bacterial growth.

The same is true for wet shaving devices, also known as safety razors/shavers. Such razor, including the razor handle, may be disposable, or alternatively, the razor may be in the form of a so-called system that comprises a reusable handle and a removable and disposable cartridge that is disposed after use and can be replaced with a fresh cartridge. Such cartridge usually includes a housing having at least one razor blade which may be disposed between a guard forward of the blade and a cap aft of the blade (in the direction of movement of the cartridge).

Cartridges for wet shaving razors often include a shaving aid body which can comprise a shaving aid material providing lubrication during shaving in wet conditions. After shaving the user typically places the razor in a wet condition on a bathroom surface. Again, fluids may drain off, or water may accumulate between the shaving aid body and the bathroom surface. Due to extended water exposure, the shaving aid material may soften and the wear rate, thus, reduced. Also, the shaving aid material at the area of contact with the bathroom surface can leave residues on the surface and can undesirably adhere the razor to the horizontal surface.

It is an object of the present disclosure to provide a personal guidance system which overcomes at least one of the above-mentioned drawbacks, in particular which provides simple coaching and monitoring, while enabling hygienic storage of the personal care implement. Further, the tool shall be suitable to be used in connection with a common manual personal care implement not comprising electronic components.

SUMMARY OF THE INVENTION

The present disclosure relates to a personal care guidance system for guiding a user through a personal care routine. The personal care guidance system comprises a personal care implement comprising a section at least partially made from a magnetic and/or ferromagnetic material, and a magnetic personal care guide to which the personal care implement is magnetically attachable and detachable. The magnetic personal care guide comprises a guidance tool, the guidance tool being activated by detaching the personal care implement from the magnetic personal care guide.

The present disclosure also relates to a magnetic personal guide, the magnetic personal guide guiding a user through a personal care routine and being adapted for releasably holding a personal care implement comprising a section at least partially made from a magnetic and/or ferromagnetic material, the magnetic personal guide comprising a guidance tool, the guidance tool being activated by detaching the personal care implement from the magnetic personal care guide.

BRIEF DESCRIPTION OF THE DRAWINGS

The invention is described in more detail below with reference to various embodiments and figures, wherein.

DETAILED DESCRIPTION OF THE INVENTION

Figure 1:
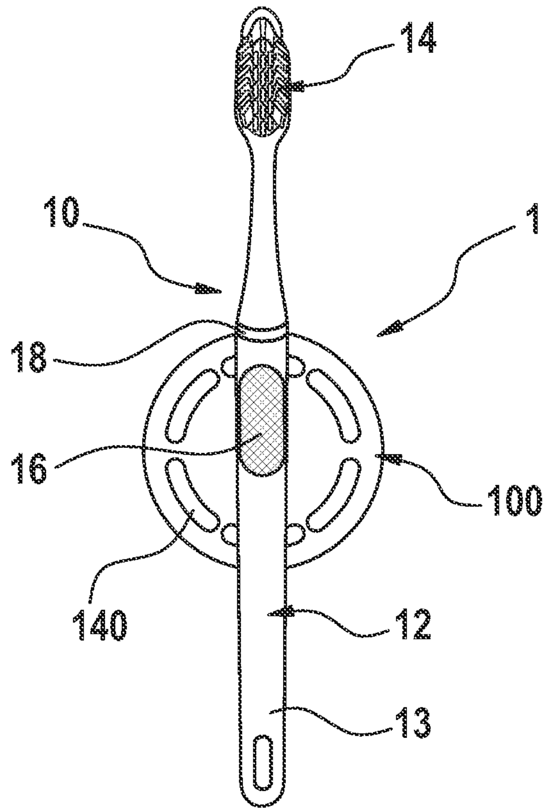
FIG. 1 shows an example embodiment of a personal care guidance system comprising a personal care implement, and a magnetic personal care guide according to the present disclosure to which the personal care implement is magnetically attached.

The present disclosure relates to a personal care guidance system for guiding a user through a personal care routine comprises a personal care implement and a magnetic personal care guide. The personal care implement is repeatedly and magnetically attachable to and detachable from the magnetic personal care guide by means of a section which is at least partially made from a magnetic and/or ferromagnetic material. The magnetic personal care guide comprises a guidance tool, the guidance tool is activated by detaching the personal care implement from the magnetic personal care guide.

The personal care implement according to the present disclosure may be any type of personal care implement, e.g. a wet shaving razor, a trimmer, a beauty device, a skin treatment device, or a manual or an electrically operated oral care implement, e.g. a toothbrush. The personal care implement may comprise a head and a handle, the head can be either permanently attached to the handle, or repeatedly attachable to and detachable from the handle.

The section of the personal care implement which is at least partially made from a magnetic and/or ferromagnetic material may be the handle, or a portion of the handle. If the handle is at least partially made from such magnetic and/or ferromagnetic material, such handle would be magnetically attachable to the magnetic personal care guide, thereby allowing for hygienic storage of the implement.

Such magnetic personal care guide may have the form of a magnetic wall holder attachable to a wall. Such wall holder is suitable/adapted to hold and store the personal care implement in a hygienic matter. The magnetic wall holder may have the form of a flat disk attachable to a wall, e.g. by means of a double-sided adhesive tape, for secure and hygienic storage of the personal care implement. Such flat disk may represent an easy to clean surface. The flat disk may comprise at least partially a TPE layer to enhance friction between the personal care implement and the magnetic guide. The disc may have a circular shape with a diameter of from about 30 mm to about 70 mm, or from about 40 mm to about 60 mm, or from about 50 to about 55, or about 52 mm. Such dimensions provide the disk with convenient attachment properties (i.e. being large enough for easy attachment), while also being small enough to not occupy too much space.

Alternatively, the magnetic personal care guide may have the form of a magnetic stand, for example, to which the magnetic section of the personal care implement is repeatedly magnetically attachable and detachable. The magnetic stand can be adapted to be placed on a surface, e.g. on a bathroom surface.

After use of the personal care implement, e.g. under wet conditions and/or in a wet environment, users tend to place or store the wet personal care implement on a horizontal surface such as a bathroom vanity, the rim of a bathtub or a shelf of a cabinet. When rested as such, the head of the personal care implement is typically in contact with the resting surface which may cause issues. For example, if a wet shaver is placed in wet conditions on a resting surface, water may drain off, and a portion of water may be retained between the head/cartridge and the horizontal surface. Shaving cartridges typically contain a shaving aid/lubrication strip. Extended exposure to water can soften the shaving aid material, and, thus, the shaving aid material can be worn out quickly. Consequently, the lifetime of the overall cartridge can be reduced. Also, residual shaving aid material at the area of contact with the resting surface can soil the resting/bathroom surface.

Likewise, if the head of an oral care implement is placed under wet conditions on a bathroom surface, bacterial growth is supported, and, thus, the oral care implement may be rendered unhygienic relatively quickly, i.e. after a relatively short period of use time. However, if a personal care implement according to the present disclosure is magnetically attached to a magnetic wall holder or stand, such negative effects can be avoided. If the oral care implement is magnetically attached to the magnetic guide, remaining water, toothpaste slurry and saliva can drain off from the oral care implement. The oral care implement can dry relatively quickly. Consequently, bacteria growth can significantly be reduced, thereby rendering the oral care implement more hygienic. Also, in contrast to a common toothbrush being stored in a toothbrush beaker where drained fluids get collected and accumulated at the bottom of the beaker, the personal care implement according to the present disclosure can be exposed to wet conditions over a significantly shorter period of time.

According to the present disclosure, the head of the personal care implement, however, is not limited to a shaver cartridge, or a toothbrush head, but can be any type of head, e.g. a beauty tool, e.g. a massaging brush or nail polisher, a skin treatment device, or another oral-care head, including but not limited to a interdental or toothpick, tongue/tissue-cleaner, and chemistry-applicator. A brush head may comprise at least one tooth cleaning element, e.g. a tuft of bristles and/or an elastomeric element, fixed to a mounting surface of the head.

The personal care implement may be an oral care implement comprising a handle and a head on which at least one tooth cleaning element, e.g. a tuft of bristles and/or an elastomeric element, may be fixed. The head can be repeatedly attachable to and detachable from the handle. While the head can be made of a non-magnetic or non-ferromagnetic material, the handle can be made from a magnetic and/or ferromagnetic material. For example, the head may be injection molded from a thermoplastic polymer, e.g. polypropylene. The oral care implement may be a manual toothbrush. The oral care implement may also be an interproximal pick, a plaque scraper or tissue/tongue cleanser.

The head of the personal care implement may be attachable to the handle via a snap-fit locking mechanism. For example, the handle may comprise a connector which may be insertable into a hollow portion in the head, or the head may comprise a connector insertable into a hollow portion in the handle. Alternatively, a connector may be provided as a further, i.e. separate part of the personal care implement. Such connector may be insertable into a hollow portion in the handle and into a hollow portion the head, respectively, thereby providing a sufficiently strong connection and stability between the head and the handle to enable a user to perform a brushing action, for instance.

Due to the provision of a magnetic/ferromagnetic section in the personal care implement, a user only needs to bring the personal care implement in close proximity to the magnetic personal care guide, and then the personal care implement gets attached automatically. No precise positioning or threading as, e.g. with common toothbrush holders, is required.

If magnetic properties are merely provided in the handle of the personal care implement, for example, and not in the head, the head portion cannot accidentally be attached to the magnetic personal care guide, thereby reducing the risk that the personal care guide gets soiled, thereby potentially reducing its functionality.

According to the present disclosure, the magnetic personal care guide comprises a guidance tool, the guidance tool being activated by detaching the personal care implement from the magnetic personal care guide. For that purpose, the magnetic personal care guide may comprise a printed circuit board assembly (PCB-A), preferably a battery-driven printed circuit board assembly (PCB-A), comprising a microcontroller. The magnetic personal care guide may further comprise means for detecting the presence of the personal care implement. The means for detecting the presence of the personal care implement may be a Hall sensor, a Reed contact sensor, a switch, a light sensor, a proximity sensor, a stress-strain gauge, FRID tag, a micro-switch and/or a movable magnet exhibiting a signal detectable by the microcontroller. Such means for detecting the presence of the personal care implement enable a seamless, noiseless, and effortless activation and deactivation of the guidance tool of the magnetic personal care guide by just removing/detaching and returning/attaching the personal care implement from and to the magnetic personal care guide.

The guidance tool may comprise a head exchange reminder function reminding a user to exchange the head of the personal care implement or the overall personal care implement after a pre-defined period of time. The guidance tool may comprise further reminder functionalities reminding a user to perform a certain action, e.g. to floss the teeth, rinse the mouth, or exchange a shaving cartridge.

If the personal care implement comprises a head repeatedly attachable to and detachable and from the handle, a high quality and relatively expensive handle of the personal care implement can be provided for usage over a longer period of time as compared to disposable personal care implements, e.g. manual toothbrushes which are discarded after about three months of use. At the same time, a relatively cheap brush refill can be exchanged on a regular basis, e.g. after about three months of use. This may provide a cost-efficient and environmentally sustainable personal care implement providing both, a high-quality handle with improved handling properties, and a solution for only purchasing a new head refill without the need to buy a respective handle, too. However, it has been seen in the past that users tend to forget to exchange the implement/head/refill after the recommended time of use which may lead to poor quality perception when using or applying a worn-out/dulled personal care implement. To overcome this drawback, the personal care guidance system may comprise a guidance tool/functionality reminding the user to exchange the implement/head after a pre-defined period of time.

For example, when it comes to oral care implements, dentists typically recommend to exchange toothbrushes/heads frequently, usually after about three months of regular use. After about three months of use, a toothbrush is typically worn out, and, thus, needs to be replaced with a fresh one to ensure that good oral health can be preserved. If a toothbrush is worn out, bristle tufts splay away, and the bending stiffness of the bristles is reduced. Such worn-out tufts cannot clean teeth thoroughly anymore, and plaque removal efficiency goes down. Bacterial may grow quicker which may cause gingivitis. Also, worn-out bristles cannot reach interdental spaces and hard to reach areas properly anymore which may result in accumulation of debris, tartar and/or plaque in these areas. If, however, the oral care implement/head gets exchanged frequently/at the right time, such negative oral health effects can be prevented.

The guidance tool may also comprise a reward system, the reward system providing feedback and/or guidance to the user after a pre-defined period of time. Such reward system may ensure and facilitate that a user uses/applies the personal care implement in the intended manner, e.g. over a pre-defined period of time. For example, if an oral care implement is concerned, such guidance tool may provide positive feedback, e.g. via indication of certain emoticons, after the user reached e.g. two-minutes brushing time.

The guidance tool may further comprise a timer that can be activated by simply detaching the personal care implement from the magnetic personal care guide. Such timer may also be pre-configured so that it is activated after a pre-defined time period after the personal care implement is detached from the magnetic personal care guide. In the following, such pre-defined period of time will be referred to as "initial intro-phase". In other words, the timer starts after a defined waiting-period, allowing the user to e.g.

moisturize the toothbrush, add toothpaste and prepare him/herself before starting the cleaning process, for example.

Such pre-defined time period may be from about 2 seconds to about 20 seconds, or from about 5 seconds to about 15 seconds, or from about 8 seconds to about 12 seconds, or about 10 seconds.

The magnetic personal care guide may comprise a timer or a clock for providing the time to the user even when the personal care implement is not detached from the guide.

The guidance tool may provide a visual, acoustic and/or haptic signal to the user as feedback and/or guidance, thereby guiding the user through a personal care routine. For users with certain disabilities a functionality allowing the user to choose the most appropriate type of signal may be beneficial. For example, if a user is blind or visually impaired, such user may choose an acoustic and/or haptic signal, instead of a visual signal, to receive feedback and/or guidance from the guidance tool.

Further, for example, a first signal may be given by the magnetic personal care guide when a pre-defined time period expired, without re-attaching the personal care implement to the magnetic personal care guide. A further, e.g. second visual, acoustic and/or haptic signal, preferably different form the first signal, may be given by the magnetic personal care guide if the personal care implement is attached to the magnetic guide before the pre-defined time period expired, thereby indicating that the personal care routine has not been fully accomplished.

In other words, if a user stops the use of the personal care implement (e.g. brushing the teeth before the pre-defined total time-range of e.g. 2 minutes ends) and re-attaches the personal care implement onto the magnetic personal care guide, a signal may be initiated. A further, e.g. different signal may be initiated if the user puts back the implement/brush after the pre-defined time-range of e.g. 2 minutes brushing time to provide a reward to the user for compliant oral care hygiene.

With such a magnetic personal care guide, a guidance system is provided that enables an effortless personal care routine/brush-coaching system. Feedback, guidance, warnings and rewards can be given to a user, even for manual devices/implements having no electronic components. At the same time, the personal care guidance system allows for convenient and hygienic storage. Use of the implement, e.g. brushing teeth can be easily monitored for transparent oral health control.

The magnetic personal care guide may comprise a housing, e.g. a watertight housing, with a small form factor, e.g. made form a hard plastic material, in which a magnet may be embedded.

The magnet may be a neodymium (NdFeB) magnet, for example. The housing may be made from thermoplastic polyurethane covering an inner frame.

The detachment and re-attachment of the personal care implement may be recognized by an energy saving sensor, for example a Reed contact sensor opening and closing an electrical circuit by applying an electro-magnetic field.

The Reed contact sensor represents an electrical switch operated by an applied magnetic field. The Reed contact sensor comprises of a pair of ferromagnetic flexible metal contacts in a hermetically sealed glass envelope. The contacts are normally open, closing when a magnetic field is present.

The use of a Reed contact sensor allows the magnetic personal care guide to recognize differences in magnetic fields by detaching and re-attaching the personal care implement's section which is at least partially made from a magnetic and/or ferromagnetic material. Attaching the personal care implement on the magnetic personal care guide causes a closed loop of magnetic field lines thereby adjusting the Reed Contact to its open position; no electrical contact is provided.

If the personal care implement is getting detached from the magnetic personal care guide, the magnetic field is getting "disturbed" by the absence of the magnetic body and the Reed Contact changes its state from open to close. This signal can be detected by the microcontroller and activates the guidance tool.

Alternatively, the detachment and re-attachment of the personal care implement can be detected by means of a movable NdFeB magnet attracting the personal care implement as primary function and connecting electrical contacts as secondary function.

The magnet may be assembled in a flexible spring construction allowing small movements towards the personal care implement when brought near to its surface while disconnecting electrical contacts or releasing micro-switches which can be used as a trigger signal enabling or disabling software functions.

The magnet, e.g. a NdFeB magnet, of the magnetic personal care guide for holding/fixing/attaching the personal care implement onto its surface and the printed circuit board assembly my be placed in a watertight housing with small and compact form-factor. The housing can be placed with double-sided adhesive e.g., on a bathroom-mirror, -tile or other wall-elements.

The magnetic personal care guide may be equipped with at least one, or with a plurality of batteries, e.g. 2× AAA batteries. These batteries can be primary or secondary cells, being charged in an external charger or being charged inside the device, for example. For example, the batteries can be charged within the magnetic personal care guide, e.g. by connecting the guide to an external power supply via a cable, e.g. USB, or by inductive/wireless charging, e.g. Qi being an open standard for wireless power transfer. The cells can be easily replaced if a bayonet lock is provided in the housing of the magnetic personal care guide, i.e. by twisting the housing in a clockwise or anti-clockwise direction. Alternatively, in order to easily open the housing of the magnetic personal care guide and for providing simple access to the batteries, a thread, a dovetail guide or a clip may be provided.

The magnet of the magnetic personal care guide may be adapted so that a pull-off force of the personal care implement perpendicular to the magnetic personal care guide is higher or about 3 N, for example.

The magnetic personal care guide may comprise at least one or a plurality of light sources, at least two light sources, six or twelve light sources. These light sources can activate at least one, or a plurality of light indication segments. The at least one light source may be a light-emitting diode (LED). The light indication segments may be used to guide a user through a personal care routine.

Such guidance process may start with removing the personal care implement form the magnetic personal care guide. The initial intro-phase may allow a user to get prepared for the use of the personal care implement, e.g. to place toothpaste on a brush head, to wet the brush head with water, before the timer starts.

The magnetic guide may comprise a plurality of light indication segments. These light indication segments can be activated one after the other, each after a pre-defined period of time to provide the user with a visual signal. The different light indication elements may be enlightened with different colors, e.g. by means of six RGB-LEDs (red, green, blue LEDs), optionally in combination with an additional white LED. Further, the different segments may pulsate to provide the user with specific information/indication/guidance.

The segments can be designed in various ways (e.g. 7-segments, icons, bars, words, etc.). The segments may be provided in a manner so that they comply with certain design rules. For example, a minimum distance between the segments may be set at about 1.5 mm.

The magnetic personal care guide may comprise a low-power display, for example at least one electro-chrome display being based on organic electrochromic polymers building a reflective display technology. Such electro-chrome displays reflect ambient light instead of backlight. Therefore, electro-chrome displays require less energy for switching their segments as compared to LC displays working on the basis of backlights. Consequently, such electro-chrome displays enable sustainable long battery life-times (0.28 μW per $cm^2$ segmented area) of the magnetic personal care guide. A set of segments can be illuminated and can appear for minutes even without voltage supply (unless "erased" with negative voltage). The electro-chrome display acts like a capacitor fading away over time. It only requires a refresh pulses every couple of minutes. Further, the electro-chrome display may be designed with relatively thin dimensions, e.g. with a thickness of about 0.3 mm and with flexible form factors regarding uneven surfaces (e.g. with a bending diameter of about 10 mm). A cover of the at least one electro-chrome display may be made from a food-compatible PET polymer. The electro-chrome display may be manufactured by means of sheet-printing which provides relatively high flexibility. As sheet-printing is relatively expensive, the electro-chrome display may also be produced by means of roll-printing as a low-cost manufacturing alternative. Alternatively, an e-ink display may be used.

For example, the magnetic personal care guide may be provided with a number of light indication segments, wherein the light indication segments are arranged in a manner creating a specific pattern. For example, as soon as the user reaches the recommended/optimal personal care routine time/brushing time of 2 minutes, the user may be informed by a visual signal or "visual reward", e.g. by a pleasant flashing of the indication segments, by rotational clock-effects in multi-colors or the like. In addition, or alternatively, an acoustic or haptic feedback and/or guidance may be given. Acoustic feedback and/or guidance may be given by a piezo buzzer, a loudspeaker, a motor resonance beep and/or a motor beep, for example. Haptic feedback and/or guidance may be given by means of motor vibration of electro-magnet vibration, for example. The magnetic personal care guide may be customizable in a manner, that the user can select the type of feedback and/or guidance by making a pre-selection of the following functionalities: visual, acoustic and/or haptic feedback/guidance. For example, the user may select "visual feedback/guidance" only, and disables "acoustic" and/or "haptic" feedback and/or guidance. Also, the user may select that only the clock is activated. This may be beneficial for advanced/experienced users which typically comply with a certain personal care routine and need only minor guidance. The time provided by the clock may be indicated on the display.

A functionality allowing to choose a certain type of signal is in particular helpful for users with certain disabilities as the user may choose the most appropriate type of signal. For example, if a user is blind or visually impaired, such user may choose an acoustic and/or haptic signal, instead of a visual signal, to receive feedback and/or guidance from the guidance tool.

Also, user feedback/guidance may be provided by means of a display displaying guidance elements, e.g. an abstract representation of brushing zones, dentition (still or animated), or comic elements, e.g. for kids training purposes. For example, such display may be a LED/TFT, LCD, OLED, e-ink display, electro chrome display or an electro fluorescence display.

The personal care guidance system may also be adapted to count the number of uses/times the personal care implement is detached and re-attached to the magnetic personal guide. For example, if a wet shaver is concerned, the number of shaving events may be tracked and indicated on the display. The number of shave events may be indicated on the display by a numerical indication. Further, if a pre-set number of shaving events has been reached, the magnetic personal care guide may provide the user with a signal that the blades of the shaver became dull, and that the shaver cartridge or the overall shaver shall be replaced with a fresh device to enable continued positive shaving experience.

If an oral care implement is concerned, the personal care guidance system may be adapted to not only track the overall lifetime of the oral care implement, but also the number of uses/cycles/times the oral care implement is detached and re-attached to the magnetic personal care guide. Certain pre-conditions may be set by the user. For example, the user may pre-set/customize the magnetic personal care guide in a way that a reminder will be given after three months of total lifetime of the brush. Three months of lifetime may be chosen because the brush may be then considered unhygienic due to bacterial growth. Likewise, the user may pre-set/customize the magnetic personal care guide in a way that a reminder will be given after e.g. 180 use cycles as the brush may be then considered as worn out (dentists usually recommend to brush teeth twice a day, and to keep a toothbrush for about three months only due to tuft wear out and bacterial growth). Depending on which pre-set condition is reached first, the guidance tool may provide the user with feedback/guidance that the implement or the head thereof shall be replaced with a fresh one.

In addition to a daily personal care routine/brushing routine, the personal care guide may be adapted to remind a user of additional tasks that typically follow a longer sequence and can, therefore, forgotten easily. For example, the personal care guide may be adapted to remind a user to floss regularly interdental areas every day/every other day or exchange a brush head every three month. The point in time for the reminder can be determined on the basis of number of brush uses, e.g. by assuming the brush is used twice per day. Alternatively, the electronics within the magnetic personal care guide may contain a real time clock, that can trigger a signal based on elapsed days. The user may be reminded with various visible or audible signals. E.g., an additional (LED) illuminated symbol can light up or a different symbol may show up on an integrated display at a given point in time. With an additional input element, e.g. a tact switch, the user can confirm that he/she followed the reminder and executed the task accordingly. After confirmation, the reminder time can be reset and counting can start again.

In addition, to improve and encourage responsible behavior in terms of sustainability, the magnetic personal care guide may provide sustainability-related reminders such as a reminder to close the running water tap while performing a personal care routine (e.g. during toothbrushing or wet shaving) by means of visible or audible signals, e.g. by an additional (LED) illuminated symbol.

In other words, the magnetic personal guide may be adapted to provide another type of signal associated with another type of personal care routine. For example, the personal care guide may guide the user through a brushing routine by providing a first type of signal after a pre-set period of time has been reached (e.g. after two minutes), while a second type of signal may be given after a pre-selected period of time has been reached, e.g. to remind a user to floss the teeth (e.g. after brushing has been completed). For example, the first type of signal may be a visual signal, while the second type of signal may be an acoustic signal. However, according to the present invention, any combination of signals could be chosen. For example, the first type of signal may be a visual signal showing a "brush" icon indicating that a brushing cycle has been completed, while the second type of signal may be a visual signal showing a "floss" icon to remind users to floss the teeth.

Such feature combination may be realized by means of an additional (tact) switch. Also, by means of such (tact) switch a user may choose from various pre-selected modes, e.g. brushing for 2 minutes for "daily clean" mode, or three minutes for "deep clean" mode. By means of another/additional (tact) switch the consumer might turn on/off additional audible feedback. If the magnetic personal guide contains an interface for wireless data exchange, the consumer/user interaction with the device can be customized in even more detail via a separate device, e.g. a smart phone with an app.

To further improve quality of guidance, the magnetic personal care guide may be adapted to enable tracking and storing data from an actual personal care routine (e.g. of a brushing or shaving routine/behavior). Based on the collected data, individualized recommendations can be provided that may help the user/consumer to improve their (daily) personal care routine, e.g. a brushing or shaving routine. Thereby, general guidance can be transformed into individual coaching. Additionally, the magnetic personal care guide may be adapted to collect data and to analyze the data in a way allowing, e.g., dentists to understand the individual brushing behavior of a user, thereby enabling professional recommendations to improve the overall oral health hygiene of the user. Likewise, by collecting and tracking water consumption data, for example, the magnetic personal care guide may be adapted to encourage positive sustainable behaviors. Also, the magnetic personal care guide may be adapted to calculate the carbon footprint and/or carbon savings for a specific personal care routine.

The magnetic personal care guide may be adapted to provide a reward system/to provide a user with rewards. For example, such reward system may enable the collection of points based on the quality of the performance of a certain personal care routine, e.g. on the basis of compliant brushing time and/or positive habits/behaviors in the area of sustainability. Such points may be exchangeable into rewards, e.g. into vouchers, discounts, and/or virtual trophies.

Further, a wireless connection for data transfer and individualization purposes may be provided within the magnetic personal care guide. For example, the magnetic personal care guide may comprise a Bluetooth or WiFi connection and/or other mesh network protocols, e.g. Thread. The magnetic guide/timer can be customized, e.g. in terms of total required brushing times, initial intro-phase, colors displayed, and pre-define time-periods of the segments. For that purpose, the magnetic personal care guide may comprise at least one button/switch to set the customized features.

In addition, the magnetic personal care guide may comprise a nightlight function and a proximity sensor and/or a watch function, e.g. by means of low-power segments like an electro-chrome display, an e-ink-display or low energy consuming LEDs.

Usually users are accustomed that products, in particular in the personal care sector, have a specific weight that guarantees high product quality and provides comfortable feeling during use of the product. The magnetic/ferromagnetic material of the handle of the personal care implement may possess a relatively high density, and, thus, a relatively heavy weight, which provides the personal care implement with such benefits. Additionally, the magnetic/ferromagnetic material of the handle may have a higher density as the non-magnetic/ferromagnetic material of the head. Consequently, the center of mass may lie within the handle which enables users to perform a well-coordinated use/brushing/shaving technique with improved sensory feeling during use/brushing/shaving.

The magnetic and/or ferromagnetic material forming at least a part of the handle may comprise an amorphous thermoplastic resin. The magnetic and/or ferromagnetic material may comprise iron oxide. In addition, the magnetic and/or ferromagnetic material may comprise aluminum oxide, boron nitride or aluminum silicate. The magnetic and/or ferromagnetic material may further comprise glass fibers which may be pre-mixed with at least a portion of the amorphous thermoplastic resin.

The amount of iron oxide used in the magnetic and/or ferromagnetic material may be up to about 70 weight percent, or up to about 67 weight percent. Iron oxide is used, such material composition provides improved magnetic properties and, thus, higher magnetic attraction forces between the personal care implement and the magnetic guide as compared to aluminum oxide, for example. Further, due to the use of iron oxide (instead of aluminum oxide), negative abrasion effects which regularly occur in molds during a molding step due to the abrasive nature of aluminum oxide can be significantly reduced.

Such magnetic/ferromagnetic material may allow for control of the weight of the handle in whatever location, e.g. by filler variation. Control of the overall personal care implement may be required due to the relatively high weight of the handle. It is now possible to use the mass/weight distribution of the material for adaption of the inertial moment of the finished implement.

The magnetic and/or ferromagnetic material may comprise from about 13 weight percent to about 30 weight percent of an amorphous thermoplastic resin; from about 3 weight percent to about 25 weight percent of aluminum oxide, boron nitride or aluminum silicate; and from about 45 weight percent to about 67 weight percent of iron oxide.

Alternatively, the magnetic and/or ferromagnetic material may comprise from about 13 weight percent to about 30 weight percent of an amorphous thermoplastic resin; and up to about 70 weight percent of iron oxide.

Such compositions provide a material density that is about three times the density of a standard plastic material used for toothbrushes, e.g. polypropylene. With the higher weight and higher thermal conductivity, the material can drive value perception, in particular in combination with a galvanic coating. Such coating may be made from real metal. The galvanic coating can be applied in a selective electroplating process. During this coating process for a multicomponent plastic part, a metallic layer is only deposited on a hard material while a further over molded soft component may remain unaffected.

The amorphous thermoplastic resin may comprise a styrene resin, e.g. styrene acrylonitrile "SAN". The amorphous thermoplastic resin may be selected from the list consisting of acrylonitrile butadiene styrene, polystyrene, and styrene acrylonitrile.

The amorphous thermoplastic resin may comprise about 17% weight percent styrene acrylonitrile, and 10.5% weight percent of a mixture comprising polybutylene terephthalate and polyethylene terephthalate.

It has been found out that such composition provides a high gravity molding material appropriate for injection molding or extrusion molding. A high specific gravity molding material high in surface hardness, excellent in coating characteristics as well as excellent in thermal conductivity can be provided.

The use of molding materials having a relatively high specific gravity is known. Such molding materials usually contain a polymeric resin and a high-density filler such as iron oxide. However, in such molding materials the amount of iron oxide which can be included is limited as the thermal conductivity properties of the molding material are relatively poor. Thus, on the one side, lower thermal conductivity leads to relatively longer cycle times during manufacturing to allow the molding material to cool after molding. On the other side, if heavy polymeric materials are filled with high heat conductive additives such as metal powder or fibers, the addition of these materials leads to tight process windows in molding because of the immediate freezing when the molten material contacts the cold wall of the tool. This fast freezing leads to high injection speed and low flow length to wall thickness ratio at the produced part.

It has been found out that the molding material as described above has a high specific gravity and optimally controlled thermal conductivity properties to reduce or expand the time needed for the molding material to cool during or after injection molding. Further, it has been found out that a relatively high percentage of iron oxide can be maintained in the molding material while improving on the thermal conductivity properties of the molding material.

The addition to aluminum oxide, boron nitride or aluminum silicate may provide the molding material with improved thermal conductivity as compared to materials containing styrene resin and iron oxide only. This improved thermal conductivity may lead to lower cycle times as the molding material may take less time to cool after molding.

Another benefit from the addition of aluminum oxide, boron nitride or aluminum silicate to the material is the ability to increase the overall amount of iron oxide in the molding material as compared to iron oxide and resins of the past. The improvements in the molding material properties come from the addition of relatively small amounts of aluminum oxide, boron nitride or aluminum silicate. The material composition comprising a relatively high percentage of iron oxide (magnetite), i.e. from about 45 weight percent to about 67 weight percent, preferably about 51 weight percent, provides good magnetic properties and a relatively heavy weight of the overall material.

Styrene acrylonitrile "SAN" provides high thermal resistance properties. The acrylonitrile units in the chain enable SAN to have a glass transition temperature greater than 100° C. The properties of SAN may allow for reduced cycle time due to relatively earlier and quicker transition temperature. Amorphous polymers are suitable for heavy resin compounds of the present disclosure due to the glass transition temperature Tg at which an amorphous polymer is transformed, in a reversible way, from a viscous or rubbery condition to a hard one. By injection molding of the heavy resin material of the present disclosure, the temperature of the material melt is above the Tg region (viscous or rubbery condition). During cooling the compound attains the high Tg temperature early and reaches dimensional stability (glassy condition). Over-molding of the heavy resin material is possible as the material stays dimensional stable due to the high Tg of the material.

Polybutylene terephthalate and polyethylene terephthalate provides the handle with high quality surface properties, including improved optical characteristics, and high impact strength. Once heated, polybutylene terephthalate and polyethylene terephthalate represent a high temperature-resistant melt having low viscosity and a high Melt Flow Index (MFI). Therefore, processability of the magnetic/ferromagnetic material during molding is improved.

The material composition may be made by blending the amorphous thermoplastic resin with powder of aluminum oxide, boron nitride or aluminum silicate with iron oxide powder. Increasing the amount of iron oxide within the material composition has further the advantage of providing a lower cost molding material as iron oxide powder is less expensive than the other filling agents. Amorphous thermoplastic resin, glass fibers, aluminum oxide, boron nitride or aluminum silicate powder and iron oxide powder may be blended by using a uniaxial extruder, a biaxial extruder, a kneader, a Banbury mixer, a roll or other such extruders. After blending, the material is heated to become flowable. The flowable material may then be molded into a handle or part of a handle by either injection molding or extrusion molding.

In an additional step, the handle or part of the handle may be electroplated to add improved appearance and a pleasant feel. Thermoplastic elastomers are well suited for electroplating as they allow for the creation of both hard and soft composite components to be electroplated selectively in one operation.

For example, the handle may comprise a thumb rest being made from a thermoplastic elastomer material and/or from a polypropylene material. These materials can be easily injection molded over the heavy resin material as discussed above. Such thumb rest may provide the handle with improved handling properties, e.g. with anti-slip properties to improve the maneuverability of the oral care implement under wet conditions, e.g. when the user brushes his teeth or performs a shaving action. The thumb rest may be made from thermoplastic elastomer material having a Shore A hardness from about 30 to about 60, or about 40 to prevent the oral care implement from being too slippery when used in wet conditions. At least a portion of the thumb rest may have a concave shape with an angle $\alpha$ with respect to the area of the remaining portion of the thumb rest from about 20° to about 25°, or about 24°. The thumb rest or a gripping region may be attached onto the front surface of the handle in the region close to the proximal end, i.e. closest to the head. The thumb rest may comprise a plurality of ribs extending substantially perpendicular to the longitudinal axis of the oral care implement. Such ribs may allow users/consumers to use the oral care implement with even more control. The user/consumer can better grasp and manipulate the handle of the oral care implement during brushing. Such handle may provide further improved control and greater comfort during brushing, in particular under wet conditions.

Furthermore, the handle may be made from at least two, or at least three different materials, each forming different parts of the handle. For example, a first material according to the present disclosure, i.e. a magnetic and/or ferromagnetic material may be injection molded into a first component of the handle thereby forming an underlying base structure of the oral care implement. A second component, e.g. of polypropylene material may be injection molded over the first component, and/or a third component, e.g. of thermoplastic elastomer material may be injection molded at least partially over the first component and/or the second component.

The third component of thermoplastic elastomer material may form the thumb rest on the front surface of the oral care implement and/or a palm grip on the back surface being opposite the front surface to be gripped by the user's/consumer's fingers and thumb. Such handle configuration may even further resist slippage during use. The thermoplastic elastomer material may extend through an aperture provided in the underlying base structure and/or second component of the handle.

Alternatively, the section of the personal care implement being at least partially made from a magnetic and/or ferromagnetic material may be a magnetic ring, sheet or clip attached to the personal care implement, a metal ring, sheet or clip attached to the personal care implement and/or a movable magnet attached to the personal care implement. As a further alternative, the personal care implement may comprise a housing, e.g. a handle housing made from magnetic metal.

The tooth cleaning elements of the oral care implement, e.g. bundle of filaments forming one or a plurality of tufts, may be attached to the head by means of a hot tufting process. One method of manufacturing the head with tufts of filaments embedded in the head may comprise the following steps: In a first step, tufts are formed by providing a desired amount of filaments. In a second step, the tufts are placed into a mold cavity so that ends of the filaments which are supposed to be attached to the head extend into said cavity. The opposite ends of the filaments not extending into said cavity may be either end-rounded or non-end-rounded. For example, the filaments may be not end-rounded in case the filaments are tapered filaments having a pointed tip. In a third step the head is formed around the ends of the filaments extending into the mold cavity by an injection molding process, thereby anchoring the tufts in the head. Alternatively, the tufts may be anchored by forming a first part of the head—a so called "sealplate"—around the ends of the filaments extending into the mold cavity by an injection molding process before the remaining part of the oral care implement is formed. Before starting the injection molding process the ends of the tufts extending into the mold cavity may be optionally melted or fusion-bonded to join the filaments together in a fused mass or ball so that the fused masses or balls are located within the cavity. The tufts may be held in the mold cavity by a mold bar having blind holes that correspond to the desired position of the tufts on the finished head of the oral care implement. In other words, the tufts attached to the head by means of a hot tufting process are not doubled over a middle portion along their length and are not mounted in the head by using an anchor/staple. The tufts are mounted on the head by means of an anchor-free tufting process.

Alternatively, the head for the oral care implement may be provided with a bristle carrier having at least one tuft hole, e.g. a blind-end bore. A tuft comprising a plurality of filaments may be fixed/anchored in said tuft hole by a stapling process/anchor tufting method. This means, that the filaments of the tuft are bent/folded around an anchor, e.g. an anchor wire or anchor plate, for example made of metal, in a substantially U-shaped manner. The filaments together with the anchor are pushed into the tuft hole so that the anchor penetrates into opposing side walls of the tuft hole thereby anchoring/fixing/fastening the filaments to the bristle carrier. The anchor may be fixed in opposing side walls by positive and frictional engagement. In case the tuft hole is a blind-end bore, the anchor holds the filaments against a bottom of the bore. In other words, the anchor may lie over the U-shaped bend in a substantially perpendicular manner. Since the filaments of the tuft are bent around the anchor in a substantially U-shaped configuration, a first limb and a second limb of each filament extend from the bristle carrier in a filament direction. Filament types which can be used/are suitable for usage in a stapling process are also called "two-sided filaments". Heads for oral care implements which are manufactured by a stapling process can be provided in a relatively low-cost and time-efficient manner.

The following is a non-limiting discussion of example embodiments of a personal care guidance system comprising a personal care implement and a magnetic personal care guide in accordance with the present disclosure, where reference to the Figures is made.

FIG. 1 shows a personal care guidance system 1 for guiding a user through a personal care routine. The personal care guidance system 1 comprises a personal care implement 10 and a magnetic personal care guide 100 to which the personal care implement 10 is magnetically attachable and detachable. The personal care implement comprises at least one section that is at least partially made from a magnetic and/or ferromagnetic material 13. The magnetic personal care guide 100 comprises a guidance tool 110 which is activatable by detaching the personal care implement 10 from the magnetic personal care guide 100.

In the present case, the personal care implement 10 is a manual oral care implement 10/toothbrush 10. However, the personal care implement 10 can be any type of implement which is able to perform or can support the performance of a personal care routine. For example, the personal care implement 10 can be a wet shaving razor, a trimmer, a beauty device (e.g. a massaging brush or nail polisher), a skin treatment device, or a manual or an electrically operated oral care implement, e.g. a toothbrush, tongue scraper, chemistry-applicator or toothpick. The personal care implement 10 may comprise a head 14—in the present case a toothbrush head 14—and a handle 12. The head 14 can be either permanently attached to the handle 14, or repeatedly attachable to and detachable from the handle 14. In the present example, the head 14 is repeatedly attachable to and detachable from the handle 12.

The handle 12 may be molded from a magnetic and/or ferromagnetic material and represents a section being at least partially made from a magnetic and/or ferromagnetic material. In addition, the handle 12 may have been undergone electroplating with any additional material, for example a polyethylene material or a thermoplastic elastomer to create a soft region, e.g. a thumb rest 16. The soft region/thumb rest 16 may improve comfort and feel of the handle 12. Alternatively, or in addition, by a further electroplating step the handle 12 may be provided with a metal layer 18 directly on the magnetic and/or ferromagnetic material to further improve the appearance of the handle 12. For example, the metal layer 18 may have the form of a ring surrounding the outer circumference of the handle 12.

Alternatively, the section of the personal care implement 10 being at least partially made from a magnetic and/or ferromagnetic material can be a magnetic ring, sheet or clip attached to the personal care implement 10, a metal ring, sheet or clip attached to the personal care implement 10 and/or a movable magnet attached to the personal care implement 10.

Figure 2:
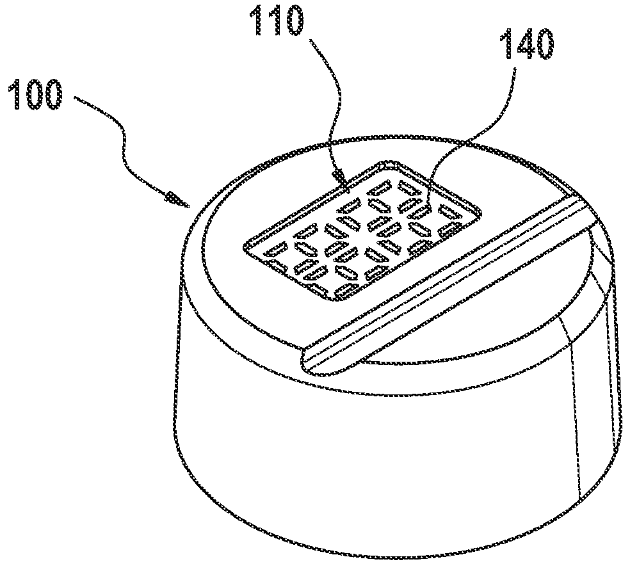
FIG. 2 shows a perspective view of a magnetic personal care guide according to the present disclosure.

The magnetic personal care guide 100 is shown in FIG. 2. The magnetic personal care guide 100 may have the form of a flat disk attachable to a wall, e.g. by means of a double-sided adhesive tape 195, for secure and hygienic storage of the personal care implement 10. The flat disk may comprise at least partially a TPE layer to enhance friction between the personal care implement 10 and the magnetic guide 100.

Figure 3:
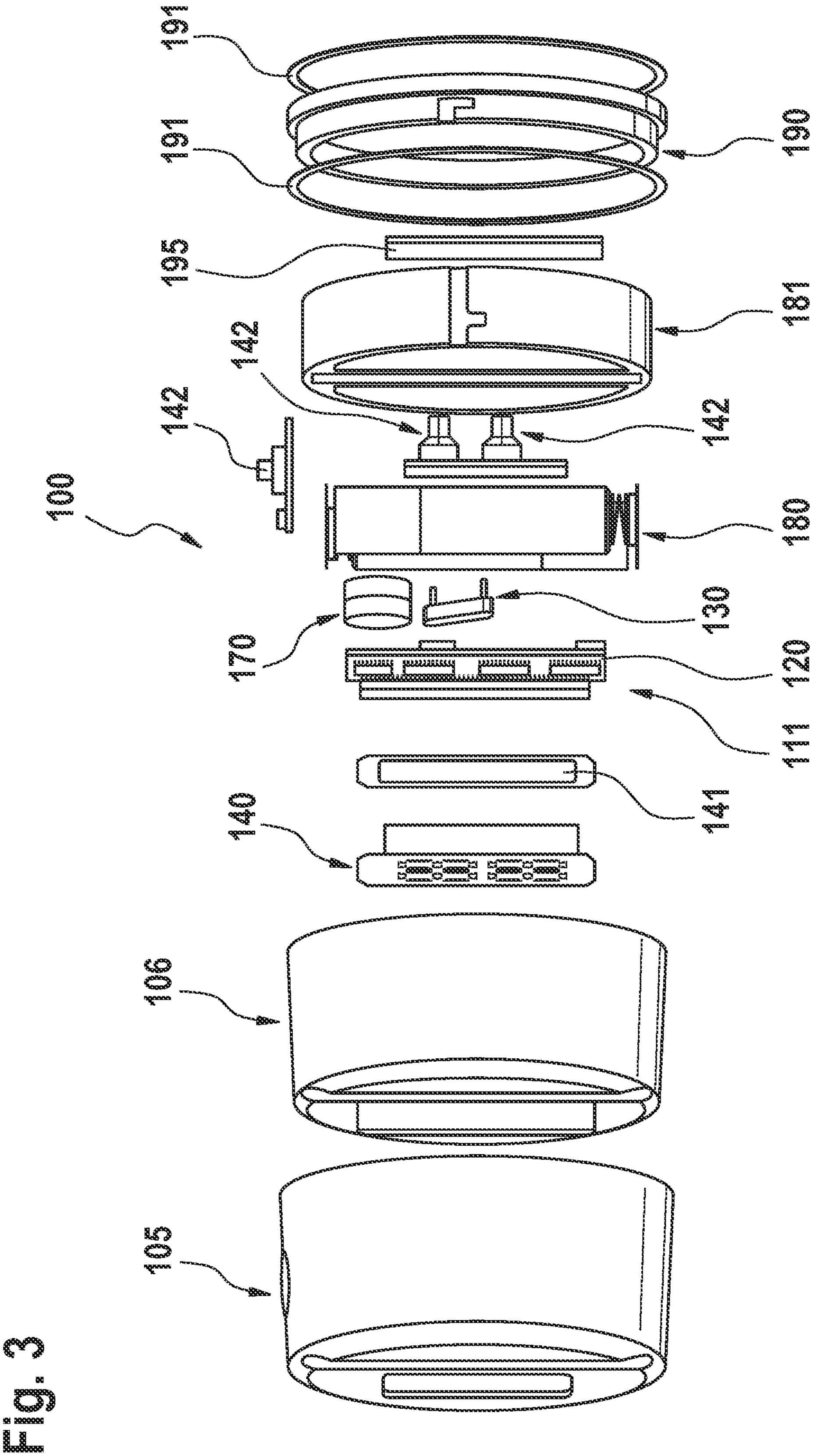
FIG. 3 shows an exploded view of the magnetic personal care guide of FIG. 2.

FIG. 3 shows an exploded view of the magnetic personal care guide 100. As derivable from FIG. 3, the magnetic personal care guide 100 comprises a magnet 170, a housing cover 105 covering an internal frame 106, and housing bottom 190 attachable to the housing cover 105 thereby providing a housing cavity, e.g. my means of a bayonet lock, screw or snap function. Sealings 191 may be provided between the housing cover 105 and housing bottom 180, as well as at the backside of the housing bottom 190. A battery-driven printed circuit board assembly (PCB-A) 111 comprising a microcontroller 120 is provided within the housing cavity. At least one battery 180 (e.g. a primary or secondary battery) or a solar-cell powering the PCB-A 111 is located in a battery compartment 181. In the present case, the battery is a primary cell, but can also be secondary cell, charged in an external charger or inside the guide 100. The magnetic personal care guide 100 further comprises means 130 for detecting the presence of the personal care implement 10. The means 130 for detecting the presence of the personal care implement 10 can be Hall sensor, a Reed contact sensor, a switch, a light sensor, a proximity sensor, a stress-strain gauge, a RFID tag, a microswitch and/or a movable magnet exhibiting a signal detectable by the microcontroller 120.

In the present embodiment, the magnetic personal care guide 100 comprises a low power display, e.g. an electro-chrome display 140 reflecting ambient light. The electro-chrome display 140 may be attached to the PCB-A via an adhesive 141. Instead of an electro-chrome display 140, the magnetic personal care guide can comprise at least one light source, e.g. at least one LED illuminating at least one or a number of light indication elements. Optionally, a real time module (not shown) can be further provided within the housing cavity to enable control and monitoring of the time expired in case the batteries 180 powering the PCB-A run out of power during a personal care routine. If new batteries are inserted, the time previously recorded will be re-displayable immediately.

Buttons/switches 142 may be provided to customize the functionalities of the guidance tool 110/magnetic personal care guide 100. For example, via buttons/switches 142 the type of feedback and/or guidance provided by the magnetic personal care guide 100 can be selected. For instance, a pre-selection of the following functionalities can be made: visual, acoustic and/or haptic feedback/guidance. For example, the user may select "visual feedback/guidance" only, and disables "acoustic" and/or "haptic" feedback/guidance. Also, via switches 142 a user may choose from various pre-selected modes, e.g. brushing for 2 minutes for "daily clean" mode, or three minutes for "deep clean" mode.

Figure 4:
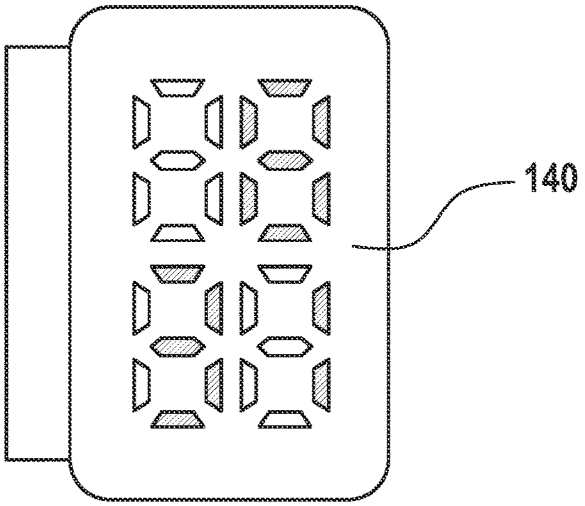
FIG. 4 shows the magnetic personal care guide of FIG. 2, the magnetic personal care guide providing a first type of signal.
Figure 5:
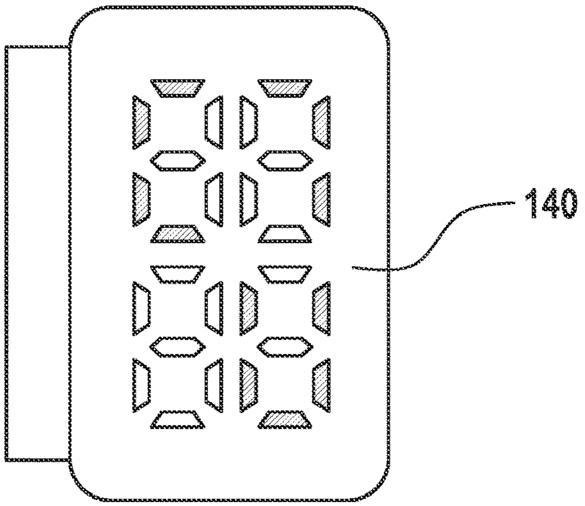
FIG. 5 shows the magnetic personal care guide of FIG. 2, the magnetic personal care guide providing a second type of signal.
Figure 6:
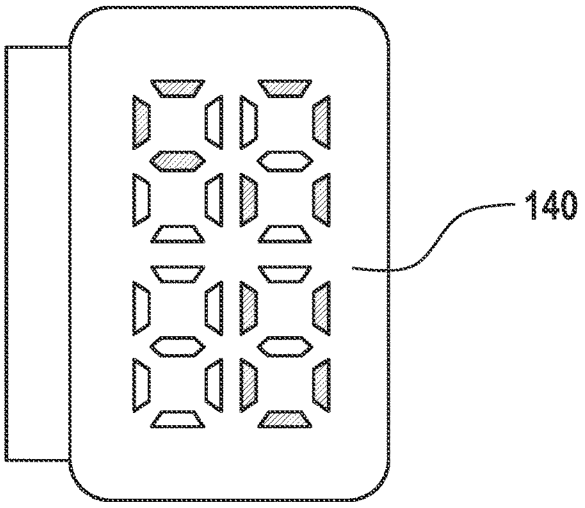
FIG. 6 shows the magnetic personal care guide of FIG. 2, the magnetic personal care guide providing a third type of signal.
Figure 7:
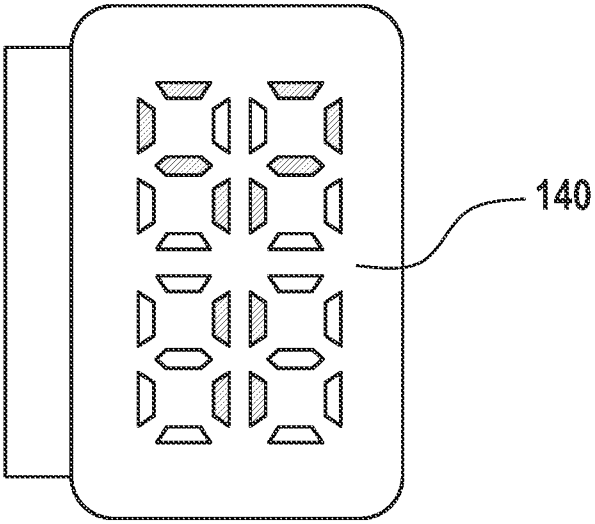
FIG. 7 shows the magnetic personal care guide of FIG. 2, the magnetic personal care guide providing a fourth type of signal.
Figure 8:
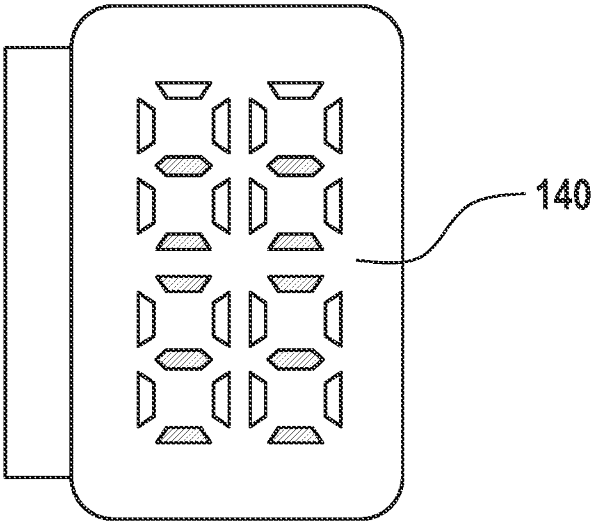
FIG. 8 shows the magnetic personal care guide of FIG. 2, the magnetic personal care guide providing a fifth type of signal.

FIGS. 4 to 8 show the display 140 of the magnetic personal care guide 100, the display 140 displaying various types of visual signals. FIG. 4 illustrates the time (in the present case 8:31). FIG. 5 illustrates a "manual brush" icon providing a signal to the user to brush/continue brushing with the manual brush. FIG. 6 illustrates a "power brush" icon providing a signal to the user to brush/continue brushing with the power brush. FIG. 7 illustrates a "wet shaver" icon providing a signal to the user to shave/continue shaving. FIG. 8 illustrates "bars" that are filling up from the bottom, indicating the time expiring during a personal care routine.

As illustrated in FIG. 8, the bars or bar segments are getting activated one after the other, each after a pre-defined period of time, when the personal care implement 10 is detached from the magnetic personal care guide 100. Said pre-defined period of time may be about 20 seconds, for example. If the display comprises six bars/bar segments, and the pre-defined period of time of enlightenment of each bar is set at 20 seconds, then the guidance process can be adapted to a recommended 2 minutes brushing time, for example.

Such timer can be pre-configured so that it is activated after a pre-defined time period after the personal care implement 10 is detached from the magnetic personal care guide 100, allowing the user to moisturize the toothbrush, add toothpaste and to prepare oneself before starting the cleaning process, for example. Said pre-defined time period can be from about 2 seconds to about seconds, from about 5 seconds to about 15 seconds, or from about 8 seconds to about 12 seconds, or about 10 seconds.

A first visual, acoustic and/or haptic signal can be given to the user by the magnetic personal care guide 100 when all bar segments have been activated/illuminated, and the pre-defined time period expired for all bar segments.

Likewise, a second visual, acoustic and/or haptic signal can be given to the user by the magnetic personal care guide 100 if the personal care implement 10 is re-attached to the magnetic personal care guide 100 before all bar segments have been activated/illuminated, or before the pre-defined time period expired for all bar segments.

Figure 9:
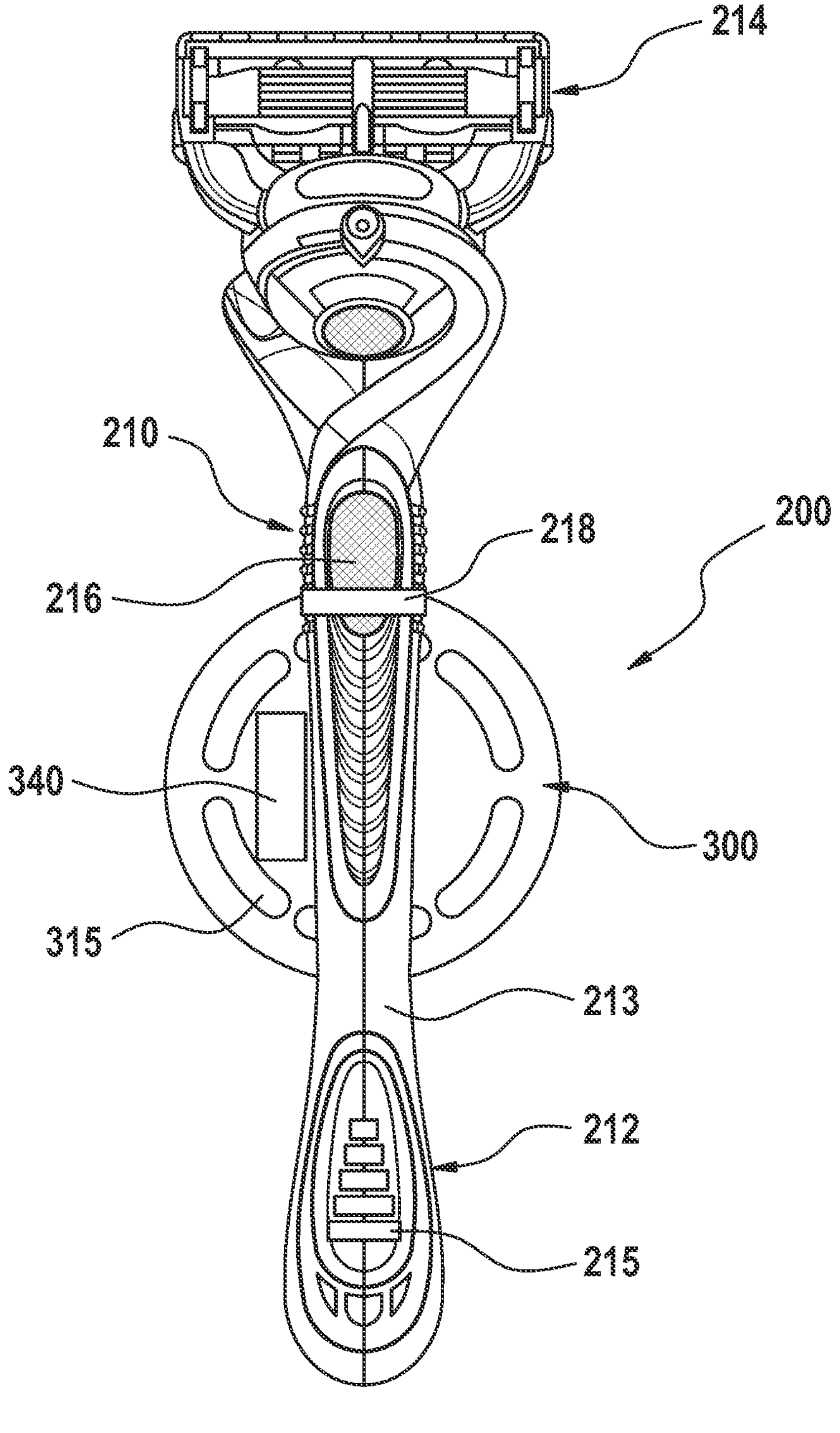
FIG. 9 shows another example embodiment of a personal care guidance system comprising a personal care implement, and a magnetic personal care guide according to the present disclosure to which the personal care implement is magnetically attached.

FIG. 9 illustrates another embodiment of a personal care guidance system 200 for guiding a user through a personal care routine. The personal care guidance system 200 may have the same functionality as the personal care guidance system 1 (FIG. 1) previously described. The system 200 may include a shaving razor 210, and a magnetic personal care guide 300 according to the present disclosure to which the shaving razor 210 is magnetically attached. The system 200 is adapted to guide a user through a personal care routine, as previously described for the system 1 of FIG. 1. The personal care guidance system 200 may include the shaving razor 210 and a magnetic personal care guide 300 to which the shaving razor 210 is magnetically attachable and detachable. The magnetic personal care guide 300 may be the same as the magnetic personal care guide 100 (FIG. 1) previously described. The shaving razor 210 may include at least one section that is at least partially made from a magnetic and/or ferromagnetic material 213. For example, the shaving razor 210 may include a handle 212 made from a magnetic and/or ferromagnetic material or contains a magnetic and/or ferromagnetic material that is inserted into the handle 212. The magnetic guide 300 may include a guidance tool 310 which is activatable by detaching the shaving razor 210 from the magnetic personal care guide 300.

The shaving razor 210 may include a head, for example a shaving razor cartridge 214. In certain embodiments, the shaving razor cartridge 214 can be either permanently attached to the handle 212, or detachable from the handle 212, thus allowing replacement with a new shaving razor cartridge 214. In the present example, the shaving razor cartridge 214 is repeatedly attachable to and detachable from the handle 212. The handle 212 may be molded from a magnetic and/or ferromagnetic material and represents a section being at least partially made from a magnetic and/or ferromagnetic material. In addition, the handle 212 may have been undergone electroplating with any additional material, for example a polyethylene material or a thermoplastic elastomer to create a soft region, e.g. a thumb rest 216. The soft region/thumb rest 216 may improve comfort and feel of the handle 212. Alternatively, or in addition, by a further electroplating step the handle 212 may be provided with a metal layer 218 directly on the magnetic and/or ferromagnetic material to further improve the appearance of the handle 212. For example, the metal layer 218 may have the form of a ring surrounding the outer circumference of the handle 212.

Alternatively, the section of the shaving razor 210 being at least partially made from a magnetic and/or ferromagnetic material can be a magnetic ring, sheet or clip attached to the shaving razor 210, a metal ring, sheet or clip attached to the shaving razor 210 and/or a movable magnet attached to the shaving razor 210.

In certain embodiments, the handle 214 (including the handle 14 shown in FIG. 1), may include one or more LEDs (light emitting diodes) 215 to communicate a status of the shaving razor 210 and/or the magnetic guide 300 (or the personal care implement 10 of FIG. 1 and magnetic guide 100 of FIG. 2). For example, the LEDs 215 may communicate a power level of the shaving razor 210 and/or the magnetic guide 300. The LEDs 215 may communicate information in regards to the physical connection between the shaving razor 210 and/or the magnetic personal care guide 300. The magnetic personal care guide 300 may also have one or more LEDs 315 to communicate information to the user.

In the present embodiment, the magnetic personal care guide 300 may include a low power display, e.g. an electro-chrome display 340 reflecting ambient light. The electro-chrome display 340 may be the same as the electro-chrome display 140 previously described. Instead of an electro-chrome display 140, the magnetic guide 300 may include at least one light source, e.g. at least one LED illuminating at least one or a number of light indication elements. Optionally, a real time module (not shown) can be further provided within the housing cavity to enable control and monitoring of the time expired in case the batteries powering the PCB-A run out of power during a personal care routine. If new batteries are inserted, the time previously recorded will be re-displayable immediately.

The shaving razor 210 may include a power source (not shown), such as one or more batteries positioned within the handle 212. The batteries may be rechargeable or alkaline batteries that can be replaced. The batteries may be charged by an electrical cable (not shown) that is plugged into the handle 212 and an external power source (e.g., wall socket or external battery pack).

In the context of this disclosure, the term “substantially” refers to an arrangement of elements or features that, while in theory would be expected to exhibit exact correspondence or behavior, may, in practice embody something slightly less than exact. As such, the term denotes the degree by which a quantitative value, measurement or other related representation may vary from a stated reference without resulting in a change in the basic function of the subject matter at issue.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

What is claimed is:

1. A personal care guidance system (1) for guiding a user through a personal care routine, the personal care guidance system (1) comprising a personal care implement (10) comprising a section at least partially made from a magnetic and/or ferromagnetic material (13), and a magnetic personal care guide (100) to which the personal care implement (10) is magnetically attachable and detachable, wherein the magnetic personal care guide (100) comprises a guidance tool (110), the guidance tool (110) being activated by detaching the personal care implement (10) from the magnetic personal care guide (100), wherein the magnetic personal care guide (100) is adapted to count a number of times the personal care implement (10) is detached and re-attached to the magnetic personal care guide (100) indicating the number of uses of the personal care implement (1).

2. The personal care guidance system (1) according to claim 1, wherein the personal care implement (10) comprises a handle (12) and a head (14), the head (14) being repeatedly attachable to and detachable from the handle (12).

3. The personal care guidance system (1) according to claim 2, wherein the guidance tool (110) comprises a head exchange reminder reminding a user to exchange the head (14) after a pre-defined period of time or number of uses.

4. The personal care guidance system (1) according to claim 1, wherein the guidance tool (110) comprises a reward system, the reward system providing feedback and/or guidance to the use after a pre-defined period of time or number of uses.

5. The personal care guidance system (1) according to claim 1, wherein the guidance tool (110) comprises a timer, the timer starting to run by activating the guidance tool (110).

6. The personal care guidance system (1) according to claim 1, wherein the magnetic personal care guide (100) comprises a clock and/or timer.

7. The personal care guidance system (1) according to claim 1, wherein the guidance tool (110) provides feedback and/or guidance to the user by means of a visual, haptic and/or acoustic signal.

8. The personal care guidance system (1) according to claim 1, wherein the guidance tool (110) provides feedback and/or guidance to the user after a pre-defined period of time after the guidance tool (110) has been activated.

9. The personal care guidance system (1) according to claim 1, wherein the guidance tool (110) comprises a printed circuit board assembly (PCB-A) (111), a battery- or solar-cell-driven printed circuit board assembly (PCB-A) (111), comprising a microcontroller (120).

10. The personal care guidance system (1) according to claim 1, wherein the magnetic personal care guide (100) comprises means (130) for detecting the presence of the personal care implement (10), the means (130) being a Hall sensor, a Reed contact sensor, a switch, a light sensor, a proximity sensor, a stress-strain gauge, a RFID tag, a micro-switch and/or a movable magnet exhibiting a signal detectable by the microcontroller (120).

11. The personal care guidance system (1) according to claim 1, wherein the personal care implement (10) comprises a handle (12), and the section of the personal care implement (10) being at least partially made from a magnetic and/or ferromagnetic material (13) is at least a portion of the handle (12).

12. The personal care guidance system (1) according to claim 1, wherein the section of the personal care implement (10) being at least partially made from a magnetic and/or ferromagnetic material (13) is a magnetic ring, sheet or clip attached to the personal care implement (10), and/or a movable magnet attached to the personal care implement (10).

13. The personal care guidance system (1) according to claim 1, wherein the guidance tool (110) is activated after a pre-defined time period after the personal care implement (10) is detached from the magnetic personal care guide (100).

14. The personal care guidance system (1) according to claim 1, wherein the magnetic personal care guide (100) comprises a low-power display (140), an electro-chrome display or an e-ink display.

15. A magnetic personal guide (100) useful for guiding a user through a personal care routine and being adapted for releasably holding a personal care implement (10) comprising a section at least partially made from a magnetic and/or ferromagnetic material (13), the magnetic personal guide (100) comprising a guidance tool (110), the guidance tool (110) being activated by detaching the personal care implement (10) from the magnetic personal care guide (100), wherein the magnetic personal care guide (100) is adapted to count a number of times the personal care implement (10) is detached and re-attached to the magnetic personal care guide (100) indicating the number of uses of the personal care implement (1).

* * * * *